United States Patent
Schneider

(10) Patent No.: US 10,091,443 B2
(45) Date of Patent: Oct. 2, 2018

(54) CAMERA SYSTEM AND METHOD FOR INSPECTING AND/OR MEASURING OBJECTS

(71) Applicant: SICK AG, Waldkirch/Breisgau (DE)

(72) Inventor: Florian Schneider, Reute (DE)

(73) Assignee: SICK AG, Waldkirch/Breisgau (DE)

( * ) Notice: Subject to any disclaimer, the term of this patent is extended or adjusted under 35 U.S.C. 154(b) by 201 days.

(21) Appl. No.: 14/873,235

(22) Filed: Oct. 2, 2015

(65) Prior Publication Data
US 2016/0105625 A1    Apr. 14, 2016

(30) Foreign Application Priority Data
Oct. 10, 2014 (EP) .................................. 14188434

(51) Int. Cl.
| | |
|---|---|
| *H04N 5/372* | (2011.01) |
| *G01J 3/46* | (2006.01) |
| *H04N 5/235* | (2006.01) |
| *G01N 21/88* | (2006.01) |
| *H04N 7/18* | (2006.01) |
| *H04N 9/04* | (2006.01) |

(Continued)

(52) U.S. Cl.
CPC ............ *H04N 5/37213* (2013.01); *G01J 3/46* (2013.01); *G01N 21/8806* (2013.01); *H04N 5/2354* (2013.01); *H04N 7/183* (2013.01); *H04N 9/045* (2013.01); *G01N 2021/845* (2013.01); *H04N 17/02* (2013.01)

(58) Field of Classification Search
None
See application file for complete search history.

(56) References Cited

U.S. PATENT DOCUMENTS

| | | |
|---|---|---|
| 2002/0181733 A1 | 12/2002 | Peck |
| 2004/0061850 A1 | 4/2004 | Fisch et al. |

(Continued)

FOREIGN PATENT DOCUMENTS

| | | |
|---|---|---|
| JP | S53-119623 A | 10/1978 |
| JP | 5-48958 A | 2/1993 |

(Continued)

OTHER PUBLICATIONS

Office action issued in corresponding Japanese application No. 2015-175370 dated Oct. 4, 2016.

*Primary Examiner* — Janese Duley
(74) *Attorney, Agent, or Firm* — Nath, Goldberg & Meyer; Jerald L. Meyer; Stanley N. Protigal

(57) ABSTRACT

The invention relates to a camera system for inspecting and/or measuring objects in an environment, comprising a color image sensor, an objective arrangement in front of the color image sensor for imaging an object from the environment on the color image sensor and at least one taking illumination light source with which the environment can be illuminated by non-monochromatic light, in particular without passing through the objective arrangement. In accordance with the invention, an internal reference illumination light source is provided which is arranged such that the color image sensor can be illuminated by it without the light irradiated by it for this purpose passing through the objective arrangement. The invention furthermore relates to a method for inspecting and/or measuring objects using such a camera system.

14 Claims, 1 Drawing Sheet

(51) Int. Cl.
*H04N 17/02* (2006.01)
*G01N 21/84* (2006.01)

(56) References Cited

U.S. PATENT DOCUMENTS

| | | |
|---|---|---|
| 2006/0251408 A1 | 11/2006 | Konno et al. |
| 2008/0106602 A1* | 5/2008 | Nussbacher ......... H04N 17/002 348/187 |
| 2010/0060755 A1 | 3/2010 | Wang |
| 2013/0088148 A1* | 4/2013 | Hessling ............ H05B 33/0854 315/77 |
| 2013/0120565 A1* | 5/2013 | Wilks ...................... G01S 7/497 348/135 |
| 2014/0030670 A1* | 1/2014 | Wong ........................ G01J 3/46 433/29 |
| 2015/0015776 A1* | 1/2015 | Rothuys ................. G03B 15/00 348/370 |
| 2015/0130958 A1* | 5/2015 | Pavani ................... H04N 9/646 348/217.1 |
| 2015/0222798 A1* | 8/2015 | Fuchikami ............... G01C 3/06 348/135 |

FOREIGN PATENT DOCUMENTS

| | | |
|---|---|---|
| JP | 2002-320231 A | 10/2002 |
| JP | 2003009162 A | 1/2003 |
| JP | 2004056531 A | 2/2004 |
| JP | 2008-275487 A | 11/2008 |
| JP | 2011-13300 A | 1/2011 |
| JP | 2014-62862 A | 4/2014 |

* cited by examiner

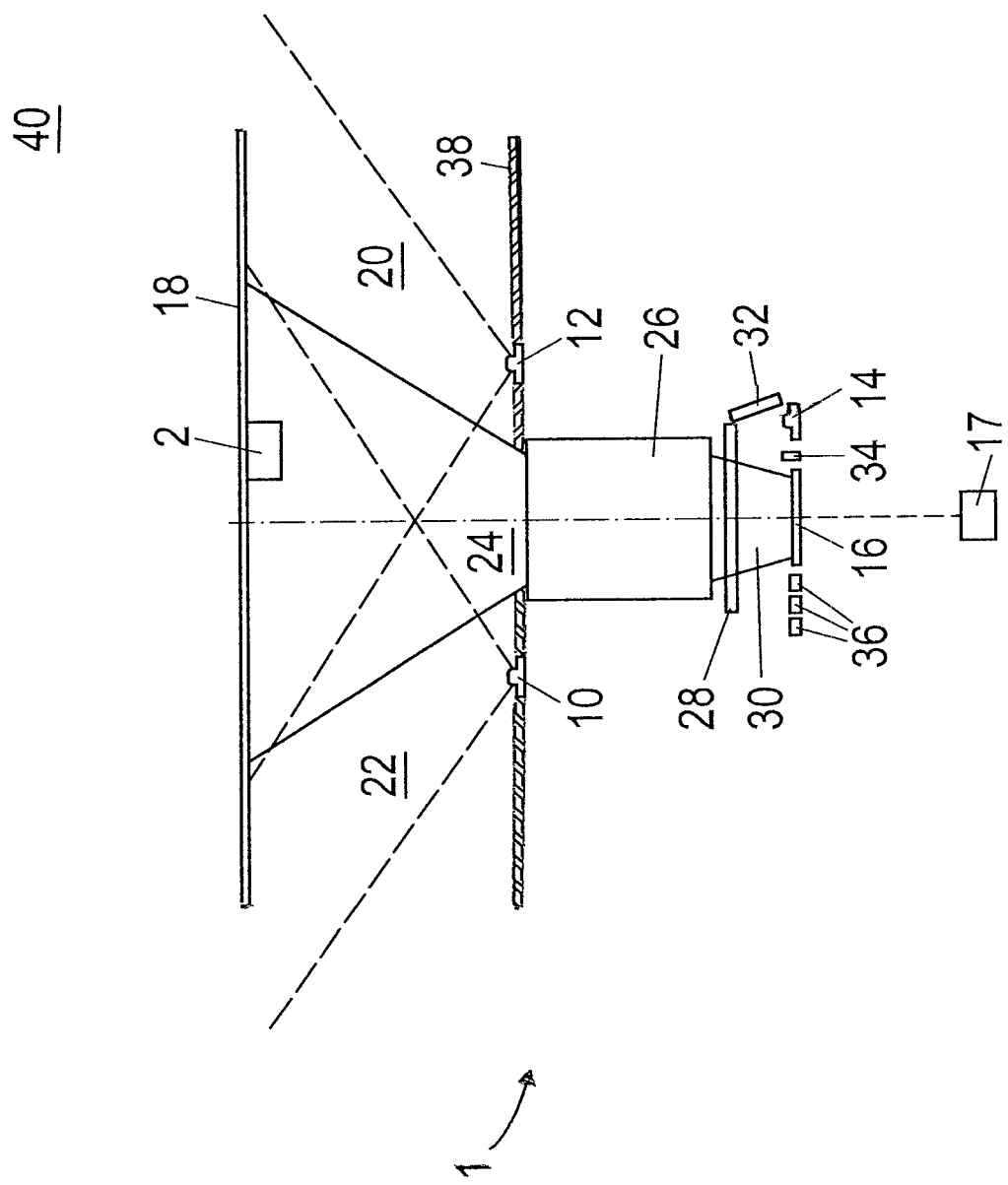

CAMERA SYSTEM AND METHOD FOR INSPECTING AND/OR MEASURING OBJECTS

The invention relates to a camera system for inspecting and/or measuring objects in an environment, comprising a color image sensor, an objective arrangement in front of the color image sensor for imaging an object from the environment on the color image sensor and at least one taking illumination light source with which the environment can be illuminated by non-monochromatic light. The invention furthermore relates to a method which is carried out using such a camera system.

The term inspecting or measuring is to be understood in this respect such that the presence or absence, the dimensions or physical properties such as the color are determined.

Camera systems are increasingly used in the inspection and measurement of objects. When it is in this respect a case of inspection applications with color image sensors which allow the color of the objects to be reproduced in three channels (red, green, blue), a white balance has to be carried out (that is a teaching of the transmission spectra and/or a taking into account of the spectrally different image sensor sensitivities) to ensure the correct capturing of the color hues. This is in particular necessary because e.g. the different illumination LEDs have different optical power densities for different wavelengths and, on the other hand, the quantum yield of an image sensor can be of different levels for different color channels.

A reference object which has a homogeneous remission is typically introduced into the environment detected by the camera system for the white balance. In such a process, an image of the reference object is taken and subsequently the three color channels of the image sensor (red, green, blue) are brought to a uniform signal level by an individual gain or by an individual offset. In later operation, each taken image is then corrected by corresponding values to obtain a color fidelity which is as good as possible. The influence of the environmental light can be calculated out or taken into account after taking a plurality of images with and without camera lighting. To this extent, the color fidelity of such camera systems is dependent on the quality of the white balance and in particular also on the stability of the spectral illumination properties. The illumination properties can, however, in particular change during operation.

An aging of the illumination LEDs used can thus occur in operation. If therefore in particular a plurality of LEDs (red, green and blue) are used, an individual aging of the conversion efficiency between electrons in photons can occur for the three different color channels. If, on the other hand, a white LED is used as the illumination LED, a shift of the spectrum can take place, in particular to longer wavelengths.

Temperature effects can also result in a spectral shift. On a use of a plurality of illumination LEDs (red, green, blue), an individual temperature dependence of the conversion efficiency for the three different color channels can occur. On a use of a white light LED, a shift of the blue peak can here in particular take place in the direction of longer wavelengths.

On the other hand, the environmental light (that is the extraneous light spectrum) can also vary. An influence of sunlight dependent on the time of day, an aging or a replacement of artificial environmental lighting or a switching on or off of lamps in the environment can e.g. thus occur.

To take account of these effects, the time-consuming white balance with reference objects has to be repeated cyclically over and over again also during the actual measurement, whereby the measurement is significantly delayed.

It is the object of the invention to provide a camera system and a method for inspecting and/or measuring objects which has a small dependence on temperature and aging.

This object is satisfied by a camera system having a color image sensor, an objective arrangement in front of the color image sensor for imaging an object from the environment, at least one taking illumination light source which can be illuminated by non-monochromatic light, and at least one internal reference illumination light source arranged such that the color image sensor can be illuminated without the light passing through the objective arrangement. Intermediate images or part images are cyclically taken during operation under illumination of the color image sensor only by the internal reference illumination light source and without illumination by the taking illumination light source. The intermediate images or part images are put into relation with images which are taken under illumination by the taking illumination light source in order to correct aging and temperature effects of the taking illumination light source.

In the camera system in accordance with the invention, at least one internal reference illumination light source is provided in addition to the taking illumination light source and is arranged such that the color image sensor can be illuminated by the internal reference illumination device without the light irradiated by it passing through the objective arrangement.

In one embodiment also the non-monochromatic light with which the environment is illuminated by the at least one taking illumination light source, does not pass through the objective arrangement.

It is possible with a camera system in accordance with the invention—such as is described below—to dispense with a white balance which has to be carried out repeatedly and/or to take account of the aging and temperature influences.

A method in accordance with the invention is carried out using a camera system in accordance with the invention.

Provision is thus made for the carrying out of a first method in accordance with the disclosed technique that cyclic intermediate images or intermediate part images are taken during the actual operation while only illuminating the color image sensor with the at least one internal reference illumination light source and without illumination by the at least one taking illumination light source and are put into relation with images which are taken with the at least one taking illumination light source (optionally without illumination by the internal reference illumination light source). This allows the aging and temperature effects of the at least one taking illumination light source to be corrected in a simple manner since the same aging effects are to be expected on an equal load on the taking illumination light source and on the reference illumination light source. In addition, the illumination light sources are as a rule exposed to the same temperature influence. A change in the spectral properties of the taking illumination light source is therefore also reflected in the same manner in the reference illumination light source. The influence of the aging and of the temperature of the taking illumination light source can therefore in particular be taken into account in a simple manner by a cyclic change between an illumination of the environment by the taking illumination light source and by an illumination only by the reference illumination light source which is provided within the camera system. The influence of the temperature or of the aging can then e.g. be calculated out in a corresponding evaluation device for images which are taken under illumination by the taking illumination light source, said influence being reflected in the same manner in both illumination light sources.

It is particularly advantageous if the internal reference illumination light source and the at least one taking illumination light source are of mutually the same construction, preferably even of the same batch. It is ensured in this manner that the environmental influences of e.g. the temperature or the aging have the same effect in both illumination light sources.

Although this means a greater effort, the environmental influence of the temperature or of the aging can, however, also be taken into account with different illumination light sources if e.g. the environmental influences on the internal reference illumination light source are known.

Another embodiment provides that both the taking illumination light source and the reference illumination light source are formed by at least one LED which are simple and inexpensive. A respective white light LED is preferably used which allows a simple construction.

In principle, however, a respective at least three individual light sources which in particular irradiate red, green and blue light to simulate white light can also be provided for the at least one taking illumination light source and the at least one reference illumination light source.

The color image sensor which is used in the camera system in accordance with the invention can e.g. be formed by a correspondingly designed color-sensitive CCD array. Alternatively, the color image sensor can also comprise a plurality of photodiodes which preferably detect different wavelengths due to correspondingly prepositioned color filters (red, green and blue).

To allow the taking into account of the environmental influences without a large calculation effort, the color image sensor should be illuminated as spectrally homogeneously as possible by the internal reference illumination light source. Otherwise, conversion functions are necessary for the different spectral degrees of illumination.

The reference illumination light source is advantageously arranged in direct proximity to the color image sensor for this purpose.

It is thus additionally ensured that the optical irradiation of the image sensor by the reference illumination light source is very high due to the spatial proximity so that environmental influences can only have a smaller influence—in particular also because the illumination time can be kept short on a shot under illumination by the reference illumination light source.

Alternatively or simultaneously, provision is advantageously made that the internal reference illumination light source is positioned or its design is configured such that the color image sensor is spectrally homogeneously illuminated. Additional diffusers can optionally be used here or the residual reflection of an optical filter optionally provided in the camera system can be utilized to ensure the homogeneous illumination of the color image sensor by the light of the reference illumination light source.

The construction becomes even simpler when no optical elements which are to be irradiated are located in the optical path between the at least one internal reference illumination light source and the color image sensor so that such elements cannot have any influence on the influences of temperature or aging.

An evaluation unit is advantageously provided in the camera system in accordance with the invention which is designed to read out and to put into relation with one another at least two kinds of signals of the color image sensor, which are included in the following group: (i) signals which are received by the at least one taking illumination light source (optionally without illumination by the reference illumination light source); (ii) signals which are received without illumination by the at least one taking illumination light source and without illumination by the at least one internal reference illumination light source; and (iii) signals which are only received by the at least one internal reference illumination light source. It is in particular possible in a simple manner using a camera system of such a configuration to carry out a white balance before operation.

For this purpose, a process management is disclosed, which provides that, before the operation, (i) an image is taken of a known reference object under illumination by the at least one taking illumination light source; and (ii) an image is taken of a known reference object without illumination. The influence of the extraneous light, that is of the environmental light, can first be determined by these two measurements. In addition (iii) an image is taken only under illumination by the at least one internal reference illumination light source. The properties of the objective can also be calculated out and taken into account in this manner.

Correction values for the first white balance are obtained a the result and the color properties of both the objective and of the extraneous light can be determined.

Using the camera system in accordance with the invention, it is then possible using the disclosed technique, to take intermediate images cyclically during the actual operation while illuminating the color image sensor using only the at least one internal reference illumination light source and to put them into relation with the images taken by the at least one taking illumination light source to correct aging and temperature effects of the at least one taking illumination light source during operation.

It can be of advantage in the method in accordance with the invention if in each case only the data from a part of the color image sensor are read out and the camera system in accordance with the invention is configured accordingly to be able e.g. to be suitable for a fast-changing environment or a fast-moving object.

To take account of the influence of a change of the extraneous light level or of the spectral properties of the extraneous light which may occur, cyclic light/dark images of the environment can be taken (that is with and without illumination by the taking illumination light source and without illumination by the reference light source).

An embodiment of the method in accordance with the invention can also be carried out using the camera system in accordance with the invention in which intermediate images are only taken cyclically by the at least one internal reference illumination light source during operation while illuminating the color image sensor in order, for example, to be able to correct a spatial irregularity of the spectral sensitivity of the color image sensor which may be present, with irregularity also being able to be dependent on age and temperature, for example.

A further development of the camera system in accordance with the invention provides that, in addition to the described color image sensor and behind the objective arrangement, an arrangement of light receivers of different spectral sensitivity is provided, preferably likewise in the vicinity of the color image sensor. "Behind" is to be understood here such that the light irradiated by the reference illumination light source can reach the color image sensor without passing through the objective arrangement. A simple embodiment provides an arrangement of three photodiodes with prepositioned spectral color filters (red, green and blue)

for this purpose. The spectral distribution of the light in the exposed and unexposed time periods can then be analyzed and inspected via a spectral scattered light analysis in the camera system.

Such an embodiment of the camera system in accordance with the invention makes it possible, in addition to the described process management in accordance with the invention, a further taking into account of the spectral properties of both the color image sensor and the taking illumination light source, e.g. to provide a further control possibility.

The invention will be explained in detail with reference to the enclosed schematic FIGURE. There is shown FIG. 1 a camera system in accordance with the invention.

A camera system 1 in accordance with the invention is shown schematically in FIG. 1. In this respect, an environment 40 is observed in which e.g. an object 2 is located. In the embodiment shown here, the object 2 is located on a surface 18 such as a conveyor belt or a shelf holder or similar. The camera system 1 is arranged here in a housing of which the front wall 38 is shown schematically. An aperture is located in the front wall and an objective arrangement 26 is arranged behind it which comprises one or more objectives which focus light 24 from the environment 40 so that it is incident as light 30 on the color image sensor 16. The environment 40 is in this respect illuminated with the aid of taking illumination LEDs 10, 12 which have illumination light sources 22 and 20 respectively. A different number of taking illumination LEDs can naturally also be provided.

The light 30 which is imaged on the color image sensor 16 by the objective arrangement 26 can optionally also be conducted through an optical filter 28.

The color image sensor is e.g. a color-sensitive CCD array known per se whose signals are evaluated by an evaluation unit 17. A reference LED 14 is located in the direct vicinity of the color image sensor 16 behind the objective arrangement 26 in the described embodiment of the camera system in accordance with the invention. "Behind" is to be understood here such that the light irradiated by the reference LED can reach the color image sensor 16 without passing through the objective arrangement. The light of this reference LED is directed onto the color image sensor 16 with the aid of a diffuser 32. A diaphragm 34 can be provided to restrict a direct illumination so that only that light is incident onto the color image sensor 16 which is widened by the diffuser in a manner such that a homogeneous spectral illumination of the color image sensor 16 is ensured.

Both the taking illumination LEDs and the reference LEDs are white light LEDs in the described example. In an embodiment which is not shown, these illumination light sources comprise in a manner known per se three LEDs (red, green and blue) to be able to simulate white light.

A method in accordance with the invention can be carried out as follows using the described camera system configuration in accordance with the invention.

A white balance is carried out before the actual operation of the camera system. For this purpose, an image capture of a reference object which is brought into the environment 40 is carried out with homogeneous remission. Only the illumination LEDs 10 and 12 are operated for this first image capture. The reference object can also be formed by the background, e.g. by the conveyor belt 18.

A second image capture of the same external reference object is carried out at the same position without illumination by the illumination LEDs 10, 12 and without illumination by the reference LED. The extraneous light which has to be taken into account before the actual operation can thus already be determined.

Third, before the actual operation, an image capture is carried out with the internal reference light-emitting diode 14 and without the illumination LEDs 10, 12 to determine the properties of the objective.

The possibility is obtained in this manner to determine the color properties of the objective and of the extraneous light and to fix correction values for the white balance.

To reduce the environmental influences in the third described image capture with the internal reference LED 14, the exposure time can be kept short. This is in particular possible since the optical irradiation of the image sensor 16 is very high due to the spatial proximity of the reference LED 14.

The described three image captures are available on the white balance. Due to the spectral properties of the camera illumination, of the extraneous light, of the objective transmission and of the quantum yield of the image sensor, all three color channels (red, green, blue) should be balanced. As described, for this purpose, the light image is deducted from the dark image and is normed to the same digital value by individual gain of each individual color channel.

Intermediate images are then taken cyclically with the same color image sensor 16 during the actual operation, with the internal reference LED 14 being switched on without the illumination LEDs 10, 12 lighting up. The aging and temperature effects of the reference LED 14 can be determined from the change of these intermediate images over time and the images taken by the illumination LED can be corrected in this manner.

Since the reference LED 14 and the illumination LEDs 10, 12 are of the same batch, aging and temperature influences will have the same effect so that a conclusion can be drawn on the corresponding aging and temperature effects of the illumination LEDs 10, 12 from the aging and temperature effects of the reference LED 14 and its effect on the image capture with the color image sensor 16.

The temperature influence of the reference LED can optionally also be calculated out via a relative observation of the three color channels with respect to one another.

A change of the extraneous light level and/or of the spectral properties of the extraneous light can be included via cyclic light/dark images of the environment (that is with and without illumination by the illumination LEDs 10, 12) in each case without a switched on reference LED 14. The light and dark images formed in this manner can be deducted from one another to take the extraneous light influence into account.

If the environment changes, this can be taken into account in that moving objects are directly eliminated or tracked via a corresponding image processing in the evaluation unit 17 and only the data of those objects are taken into account or the data of those objects are actually not taken into account. Another possibility provides that always only a few color image sensors are read out with and without illumination by the illumination LEDs and are deducted from one another to take the extraneous light influence into account.

It is therefore possible with the arrangement or the process management in accordance with the invention nevertheless to correct the aging and temperature effects of the illumination LEDs 10, 12 without the necessity of a cyclically repeating white balance. To take account of the influence of the possibly varying extraneous light level, only comparisons which can be carried out when changing ambient light level, which is feasible in a simple manner, so that comparisons between light and dark images are carried out cyclically.

The reference illumination light source provided in accordance with the invention can also advantageously be used in a different manner. A so-called "fixed pattern noise" (FPN) can thus thereby be corrected which is a spatial noise of the color image sensor pixels. Such a spatial noise is caused, on the one hand, by an irregularity of the dark signal ("dark signal non-uniformity") (DSNU), but also in particular by the individual pixel sensitivity ("photo response non-uniformity") (PRNU). Whereas the DSNU can be taken into account in that dark intermediate images of short exposure time are taken during operation, the PRNU can in particular be determined and corrected using the arrangement in accordance with the invention via intermediate images under illumination by the reference light-emitting diode 14. A change in the spatial sensitivity of the color image sensor e.g. for different wavelengths can be checked and adjusted during operation in this manner.

In addition to the described reference LED, photodiodes 36 with prepositioned color filters (red, green, blue) can be prepositioned in direct proximity to the color image sensor 16 which are e.g. illuminated by scattered light of the total camera system. The spectral distribution of the light in the exposed and unexposed time periods can be analyzed via a spectral scattered light analysis using such an arrangement instead of the cyclic light/dark images with the color image sensor 16 or with the reference images with the reference LED.

REFERENCE NUMERAL LIST

1 camera system
2 object
10, 12 taking LED
14 reference LED
16 CCD color image sensor
17 evaluation unit
18 surface
20, 22 illumination light cone
26 objective
28 optical filter
30 remission light
32 diffuser
34 diaphragm
36 photodiode with color filter
38 front housing wall
40 environment

The invention claimed is:

1. A method for inspecting or measuring objects, the method comprising:
   using a camera system, the camera system comprising:
      a color image sensor;
      an objective arrangement in front of the color image sensor for imaging an object on the color image sensor;
      at least one taking illumination light source with which an environment for observation can be illuminated by non-monochromatic light; and
      at least one internal reference illumination light source which is arranged such that the color image sensor can be illuminated by it without the light irradiated by it passing through the objective arrangement, wherein the at least one internal reference illumination light source and the at least one taking illumination light source are of mutually the same construction,
   the method further comprising the steps of:
      cyclically taking intermediate images or intermediate part images during operation under illumination of the color image sensor only by the at least one internal reference illumination light source during operation to take account of spatial inhomogeneities of the spectral sensitivity and without illumination by the at least one taking illumination light source; and
      putting into relation the intermediate images or intermediate part images with images which are taken under illumination by the at least one taking illumination light source in order to correct aging and temperature effects of the at least one taking illumination light source.

2. The method of claim 1, further comprising the steps of:
   (i) taking an image of a known reference object under illumination by the at least one taking illumination light source;
   (ii) taking an image of the known reference object without illumination; and
   (iii) taking an image only under illumination by the at least one internal reference illumination light source before the operation.

3. The method of claim 1, further comprising the steps of:
   cyclically taking light and dark images of the environment during operation and putting into relation the light and dark images of the environment to correct the influence of environmental light, wherein the light images are taken only under illumination by the at least one taking illumination light source and the dark images are taken without illumination.

4. The method of claim 1, further comprising the step of:
   respectively only reading out data from a part of the color image sensor.

5. A method for inspecting or measuring objects comprising: using a camera system comprising:
   a color image sensor;
   an objective arrangement in front of the color image sensor for imaging an object of an environment for observation on the color image sensor;
   at least one taking illumination light source with which the environment can be illuminated by non-monochromatic light; and
   at least one internal reference illumination light source which is arranged such that the color image sensor can be illuminated by it without the light irradiated by it passing through the objective arrangement; and using the camera system to carry out the following steps, comprising:
   taking an image of a known reference object under illumination by the at least one taking illumination light source;
   taking an image of the known reference object without illumination; taking an image only under illumination by the at least one internal reference illumination light source before operation;
   cyclically taking intermediate images or intermediate part images under illumination of the color image sensor only by the at least one internal reference illumination light source during operation to take account of spatial inhomogeneities of the spectral sensitivity; and a change in the spatial sensitivity of the color image sensor for different wavelengths can be checked and adjusted during operation.

6. The method of claim 5, further comprising the steps of:
cyclically taking light and dark images of the environment during operation and putting into relation the light and dark images of the environment to correct the influence of environmental light, wherein the light images are taken only under illumination by the at least one taking illumination light source and the dark images are taken without illumination.

7. The method of claim 5, further comprising the step of:
respectively only reading out data from a part of the color image sensor.

8. The method of claim 1,
wherein the at least one taking illumination light source and the at least one internal reference illumination light source are each formed by at least one LED.

9. The method of claim 1,
wherein the at least one taking illumination light source and the at least one internal reference illumination light source are each formed by at least one white light LED.

10. The method of claim 1,
wherein the at least one taking illumination light source and the at least one internal reference illumination light source each comprise at least three individual light sources.

11. The method of claim 1,
wherein the at least one internal reference illumination light source is configured and arranged such that it illuminates the color image sensor with spectral homogeneously.

12. The method of claim 1,
wherein no optical elements to be irradiated through are located in an optical path between the at least one internal reference illumination light source and the color image sensor.

13. The method of claim 1, further comprising:
reading out and comparing at least two kinds of signals of the color image sensor, the signals comprising one or more of the group consisting of:
(i) signals received under illumination by the at least one taking illumination light source;
(ii) signals received without illumination by the at least one taking illumination light source and without illumination by the at least one internal reference illumination light source; and
(iii) signals received only by the at least one internal reference illumination light source.

14. The method of claim 1, further comprising:
reading out and comparing at least two kinds of signals of the color image sensor, the signals comprising one or more of the group consisting of:
(i) signals received under illumination by the at least one taking illumination light source;
(ii) signals received without illumination by the at least one taking illumination light source and without illumination by the at least one internal reference illumination light source; and
(iii) signals received only by the at least one internal reference illumination light source,
wherein the at least one taking illumination light source and the at least one reference illumination light source each comprise at least three individual light sources.

* * * * *